United States Patent [19]

Leckrone

[11] Patent Number: 4,685,458

[45] Date of Patent: Aug. 11, 1987

[54] ANGIOPLASTY CATHETER AND METHOD FOR USE THEREOF

[75] Inventor: Michael E. Leckrone, Indianapolis, Ind.

[73] Assignee: Vaser, Inc., Indianapolis, Ind.

[21] Appl. No.: 739,986

[22] Filed: May 31, 1985

Related U.S. Application Data

[62] Division of Ser. No. 585,112, Mar. 1, 1984, Pat. No. 4,627,436.

[51] Int. Cl.$^4$ ............................................. A61B 17/38
[52] U.S. Cl. .................................. 128/303.1; 128/305
[58] Field of Search ............... 128/303.1, 303.15, 304, 128/305, 401, 6, 751, 752; 604/101

[56] References Cited

FOREIGN PATENT DOCUMENTS 2804015  8/1979  Fed. Rep. of Germany ...... 128/305
938977   7/1982  U.S.S.R. .............................. 128/305

*Primary Examiner*—Lee S. Cohen
*Attorney, Agent, or Firm*—Kenyon & Kenyon

[57] ABSTRACT

The disclosure relates to a device for use in removing undesired material from a duct within a patient's body. The device comprises a catheter adapted to be disposed within a duct and an element disposed adjacent to the distal end portion of the catheter such as a fiber optic emitting laser energy, a heated element or a knife for intersecting and releasing the undesired material. The undesired material may be an occlusion or an accumulation of plaque within a blood vessel. An inflatable bladder is provided for positioning the distal end portion of the catheter adjacent the inner surface of the duct to maintain the element for intersecting and releasing the undesired material adjacent thereto. The device can also include a pair of abutments disposed adjacent the distal end portion of the catheter to form a chamber adjacent the inner surface of the blood vessel and prevent the escape of laser energy after it has been applied to the undesired material.

14 Claims, 14 Drawing Figures

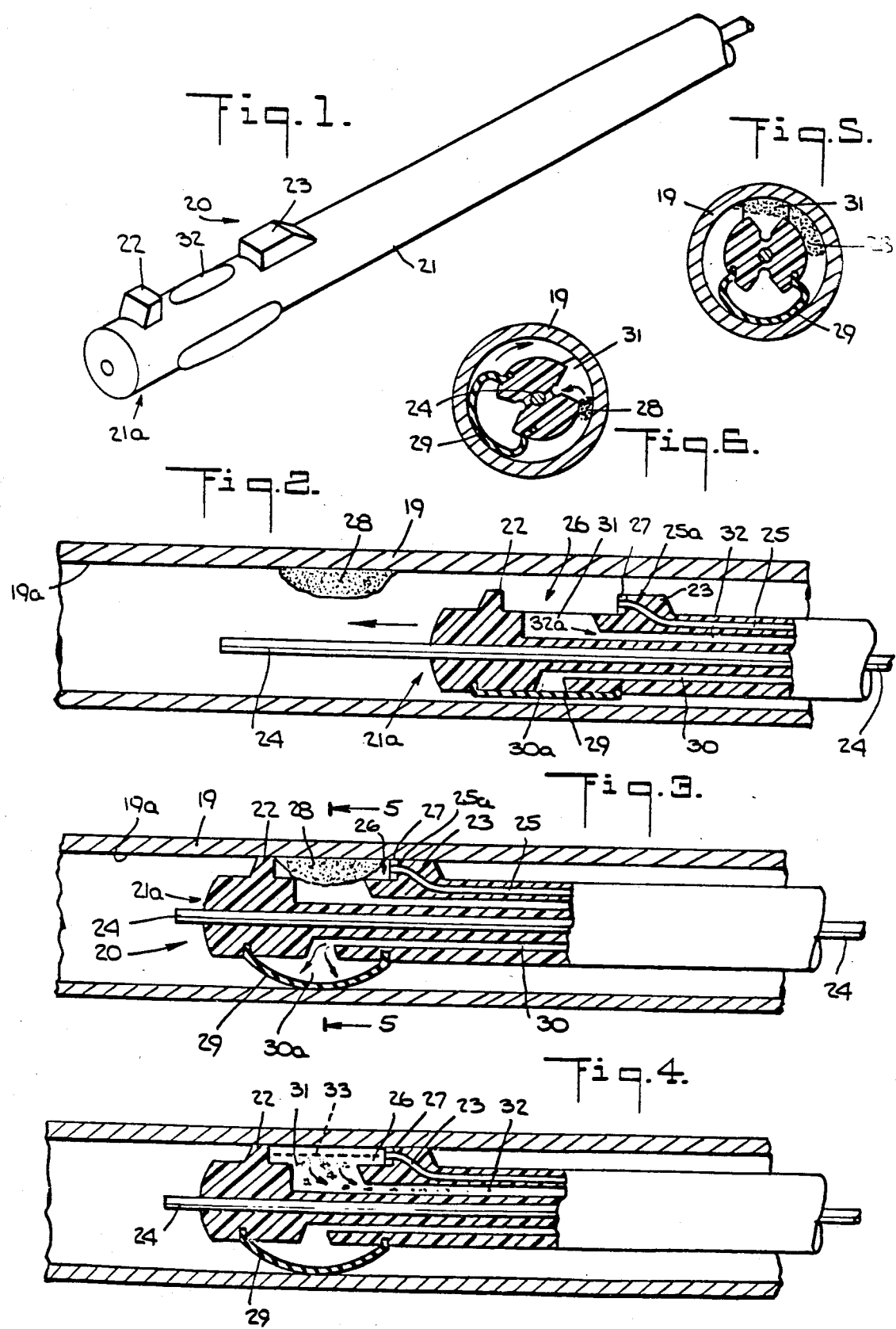

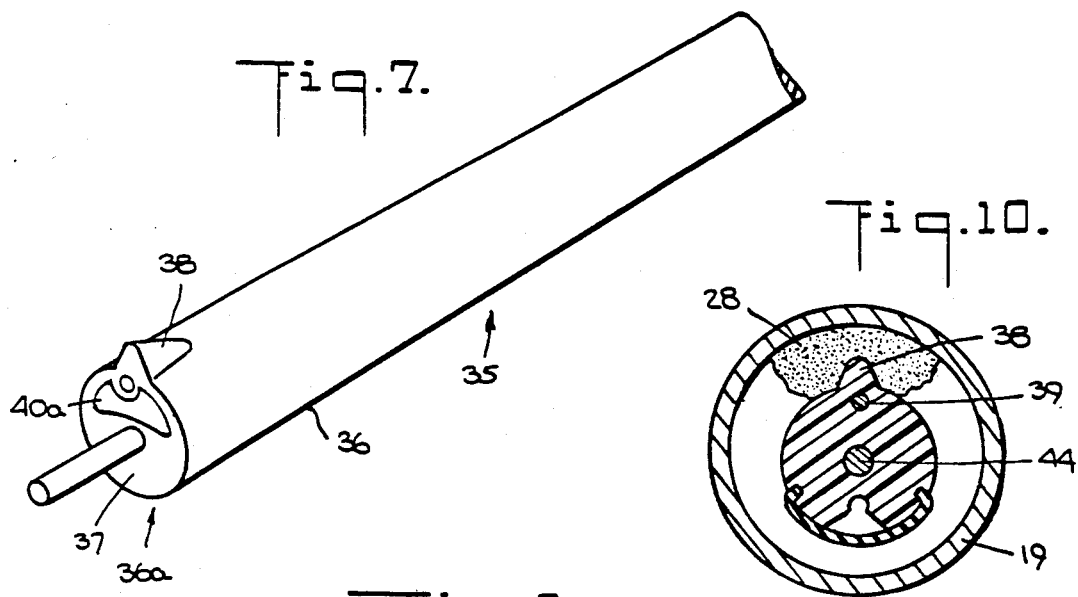
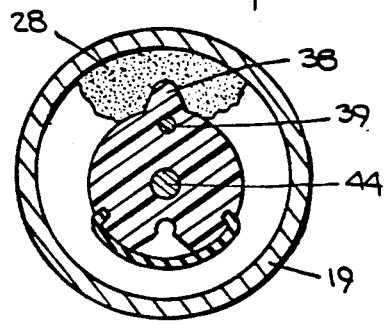
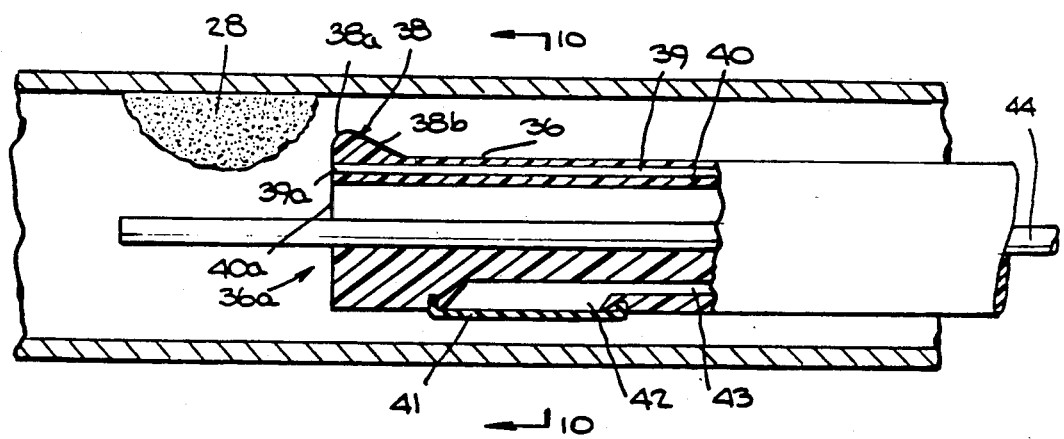
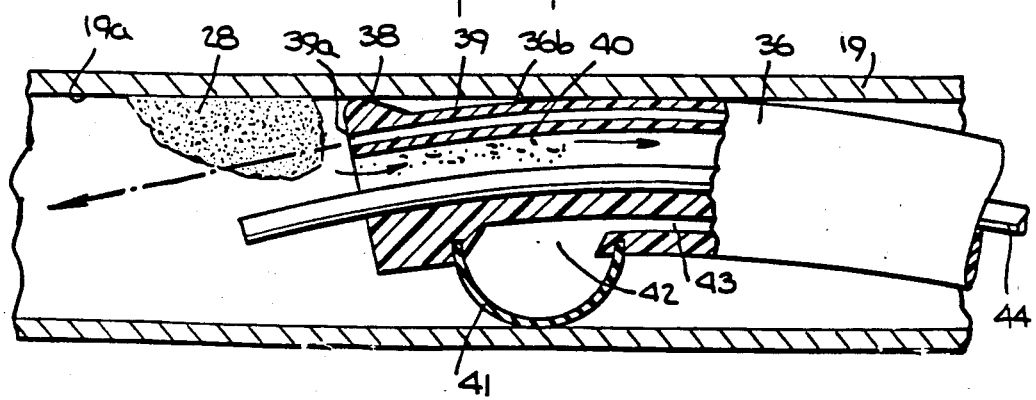

ANGIOPLASTY CATHETER AND METHOD FOR USE THEREOF

This is a division of application Ser. No. 585,112 filed Mar. 1, 1984, now U.S. Pat. No. 4,627,436.

BACKGROUND OF THE INVENTION

1. Field of the Invention

The invention relates to catheters which are adapted to be inserted in ducts and passages within the body as well as blood vessels including arteries and veins for the removal of blockages, obstructions, occlusions, etc. or the like therein. More in particular, the invention relates to laser angioplasty, the use of a laser to vaporize plaque in coronary, femoral and other arteries. Laser angioplasty comprises the directing of a catheter which is adapted to transmit a laser beam, i.e., laser energy, into a blood vessel and advancing the free end of the catheter within the blood vessel to the location of an occlusion or arteriosclerotic plaque within the blood vessel. The catheter delivers laser energy to the location to vaporize the occlusion, thereby opening obstructed blood vessels.

The use of the intense and concentrated energy of a laser within a portion of the body such as a blood vessel presents the possibility of damage to the surrounding tissue. In the case of a blood vessel, possible perforation of the blood vessel is of chief concern.

2. Description of the Prior Art

Conventional catheters for laser angioplasty have a flexible outer tube which can be inserted into a blood vessel. Within the outer tube is disposed a bundle of optical fibers which extend to adjacent the distal end of the outer tube. A laser is connected to the bundle for transmitting laser energy to an occlusion within the blood vessel. Debris resulting from the vaporizing of the occlusion by the laser can be removed by applying suction to the outer tube.

U.S. Pat. No. 4,207,874, issued June 17, 1980, for a "Laser Tunneling Device" is an example of a catheter having a bundle of optical fibers. The catheter is adapted to be advanced within a blood vessel to adjacent an occlusion or calcified plaque for the application thereto of the energy of a laser. Suction can be applied to the laser to remove the debris resulting from the vaporization of the occlusion.

U.S. Pat. No. 4,224,929, issued Sept. 30, 1980, for "Endoscope with Expansible Cuff Member and Operation Suction", discloses an endoscope adapted to be placed in a blood vessel. A pair of cuff members spaced apart from one another and disposed adjacent the distal end of the endoscope is adapted to be expanded to contact the inner walls of the blood vessel and form a chamber between the cuff members. A procedure such as observation, surgical treatment, etc. can then be performed within the chamber formed by the cuff members with the blood vessel.

U.S. Pat. No. 4,240,431, issued Dec. 23, 1980, for "Laser Knife" discloses a device using laser energy for the incision or excision of an affected part of the body. In order to prevent the laser energy from causing undesirable cautery or piercing of normal tissue adjacent that which is to be treated, the laser energy is intercepted by a receiving surface, once the cutting procedure is completed.

SUMMARY OF THE INVENTION

The invention of a catheter device for use in removing undesired material from a duct within a patient's body comprises a catheter adapted to be disposed within a duct, means disposed adjacent to the distal end portion of the catheter for intersecting and releasing undesired material from a duct such as an occlusion or an accumulation of plaque within a blood vessel, and an inflatable bladder for positioning the distal end portion of the catheter adjacent the inner surface of the duct.

In one embodiment of the invention, a fiber optic within the catheter transmits laser energy to the distal end portion of the catheter for application of the undesired material.

In another embodiment of the invention, a pair of abutments form a chamber adjacent the inner surface of the blood vessel and prevent the escape of laser energy after it has been applied to the undesired material.

In still another embodiment, the catheter is provided with a standoff to deflect the distal end portion of the catheter to direct the laser energy away from the wall of the blood vessel.

In a further embodiment of the invention, the catheter includes an elongated element extending between abutments adjacent the distal end of the catheter for severing an occlusion or accumulation of plaque.

Therefore, it is an object of the invention to position the distal end of a catheter within a duct in a patient's body by remote control prior to the application of laser energy by the catheter.

It is another object of the invention to prevent the application of laser energy to the inner surface of the blood vessel as the laser energy is being applied to the plaque.

It is an additional object of the invention to rotate the catheter device within a blood vessel to apply laser energy to all portions of the interior of the blood vessel adjacent the distal end of the catheter.

BRIEF DESCRIPTION OF THE DRAWINGS:

FIG. 1 is a perspective view of the laser angioplasty catheter of the invention showing a pair of abutments, a suction port therebetween and an inflatable bladder;

FIG. 2 is a fragmentary vertical section of the catheter when disposed in a blood vessel adjacent to an accumulation of plaque therein;

FIG. 3 is a fragmentary vertical section of the catheter showing the abutments disposed adjacent to the plaque in the blood vessel and showing the bladder inflated;

FIG. 4 is a fragmentary vertical section of the catheter showing the application of laser energy to the plaque and the removal of the debris of the plaque by a vacuum lumen;

FIG. 5 is a vertical section taken along the line 5—5 in FIG. 3 and showing the catheter positioned by the inflated bladder within a blood vessel;

FIG. 6 is a vertical section of the catheter showing the catheter being rotated within a blood vessel;

FIG. 7 is a perspective view of another embodiment of the laser angioplasty catheter of the invention showing a standoff adjacent the distal end of the catheter for positioning the catheter within a blood vessel;

FIG. 8 is a fragmentary vertical section showinq the catheter of FIG. 7 being positioned adjacent to plaque within a blood vessel;

FIG. 9 is a fragmentary vertical section of the catheter of FIG. 7 showing the standoff urged against the inner surface of a blood vessel in response to the inflation of the bladder;

FIG. 10 is a vertical section taken along the line 10—10 in FIG. 8 showing the catheter of FIG. 7 disposed within a blood vessel prior to inflation of the bladder;

DESCRIPTION OF THE PREFERRED EMBODIMENTS

Figure 11:
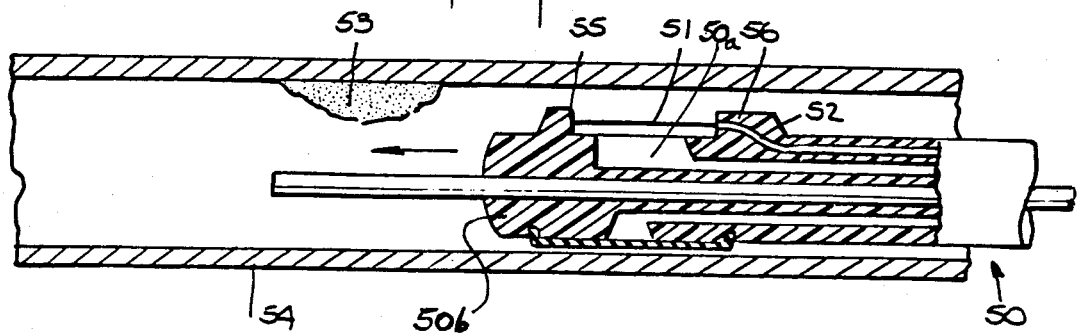
FIG. 11 is a fragmentary vertical section of another embodiment of the catheter of the invention which includes a heated element for releasing undesired material from a duct.

In FIG. 1 there is shown an embodiment of the catheter device of the invention comprising a laser angioplasty catheter device 20. Catheter device 20 includes catheter 21 having a distal end portion 21a and a proximal end portion (not shown). The diameter of the catheter is such that it can be readily introduced into and advanced along a blood vessel 19 of a patient, for example a coronary or a femoral artery. Thus the distal end portion of the catheter device is advanced along a blood vessel to the vicinity of an occlusion or an accumulation of plaque, either of which are to be removed from the blood vessel. The proximal end portion of the catheter remains external to the patient during the use of the catheter in destroying an occlusion or other lesions within a blood vessel. A pair of abutments 22 and 23 are disposed on the outer surface of catheter 21 adjacent distal end portion 21a of the catheter. The space between the abutments is adapted to form a working chamber when the catheter is positioned within a blood vessel adjacent to material such as an occlusion.

As shown in FIG. 2, catheter device 20 is provided with a filament or lumen 24 for positioning the catheter device within a blood vessel as will be described below. Filament 24 which extends along the interior of catheter 21 is free of the catheter in order that the catheter can be translated and rotated with respect to the filament. The filament can guide the catheter to the location of an occlusion by first advancing the distal end portion 24a of the filament to adjacent the obstruction to be treated. Thereafter, the catheter can be advanced along the filament until the distal end portion 21a of the catheter is adjacent to the obstruction. Since the filament within the catheter is free of the catheter, the catheter can be rotated with respect to the filament as the catheter is rotated within the blood vessel.

Further as shown in FIG. 2, there is provided fiber optic 25 having a proximal end (not shown) adapted to be connected to a source of laser energy and having a distal end portion 25a disposed within abutment 23. Typically the fiber optic can be a bundle of glass fibers or a single fiber adapted to transmit light including laser energy. By way of example, the source of laser energy may comprise a blue-green argon laser in the power range extending up to approximately twenty watts.

Laser energy emitted from the distal end portion 25a of the fiber optic is directed across chamber 26 formed between abutments 22 and 23 so that the laser energy can be intercepted and absorbed by abutment 22. In this way, the heating effect resulting from the application of laser energy is confined to chamber 26 and prevented from advancing along or into the blood vessel 25 by abutment 22.

In order to focus the laser energy into chamber 26, there may be provided refracting device or lens 27 mounted in abutment 23 at the distal end portion 25a of the fiber optic. The lens focuses and concentrates the laser energy into chamber 26 and insures that energy crossing the chamber is intercepted by abutment 22.

In FIG. 2, catheter device 20 is shown being advanced in the direction of the arrow toward plaque 28 attached to the inner surface 19a of blood vessel 19. The distal end portion 21a of the catheter is provided with bladder 29 which is shown in its relaxed position in FIG. 2. The distal end of lumen 30 extending within catheter 21 has an opening adjacent the inner surface of bladder 29. The proximal end of lumen 30 (not shown) can be connected to a suitable source of fluid pressure such as air pressure of a level which is adapted to inflate bladder 29 into the positions shown in FIG. 3.

Also shown in FIG. 2 is port, suction port 31, disposed between abutments 22 and 23. Lumen 32 has its distal end portion 32a in communication with suction port 32. The proximal end of lumen 32 (not shown) can be connected to a suitable source of pressure which is less than the ambient pressure such as a vacuum source. Accordingly, suction port 31 is adapted to receive flow from within the blood vessel and to enable such flow from within the blood vessel and to enable such flow to be transmitted by means of lumen 32.

In FIG. 3, the catheter device 20 is shown positioned within blood vessel 19 with abutments 22 and 23 positioned at the opposite sides of plaque 28 which is to be removed from the inner surface 19a of the blood vessel. The inflation of bladder 29 causes the bladder to contact the inner surface of the blood vessel and urge distal end 21a of the catheter toward the inner surface of the blood vessel opposite the inflated bladder with the result that the abutments 22 and 23 bear against the inner surface of the blood vessel at the opposite sides of the plaque 28. In this way, the plaque is substantially trapped within chamber 26 formed by the abutments.

Laser energy is then applied to fiber optic 25 and emitted at the distal end 25a of the fiber optic into chamber 26 where the laser energy encounters the plaque 28. The laser energy is adapted to heat the plaque and lead to its disintegration as the plaque tends to vaporize in response to the heating. As the plaque disintegrates, abutments 22 prevents the release of laser energy into the blood vessel in advance of the end portion of the distal end 21a of the catheter. The laser can be pulsed or can be switched in a manner to control the intensity and level of the energy being delivered to the plaque. During the application of laser energy, bladder 29 is maintained in an inflated state in order to keep the abutments against the inner surface of the blood vessel.

In FIG. 4, laser beam 33 shown by a dotted line extends across chamber 26 as the plaque is being vaporized. The laser beam after crossing the chamber is intercepted by abutment 22 which can absorb the remaining level of energy and prevent it from being transmitted within the blood vessel. The debris as shown in FIG. 4 flows in the direction of the arrows through the port and into lumen 32 in response to reduced pressure or vacuum therein, thereby removing the debris from the site of the plaque at the inner surface of the blood vessel.

In FIG. 5, the catheter device is shown positioned within blood vessel 19 with bladder 29 inflated and with plaque 28 displaced to one side of the chamber 31 formed between the abutments.

In FIG. 6, the catheter device 20 is shown being rotated in the direction of the arrow in order to position plaque 28 within chamber 31. The rotational movement of the device is caused by the application of rotational movement or torque to catheter 21. Accordingly, the catheter device can be rotated about filament 24 to sweep the complete interior of the blood vessel circumferentially and insure removal of all plaque or the like therein.

In FIG. 7, there is shown another embodiment of the laser angloplasty catheter 35 of the invention. Catheter device 35 comprises catheter 36 having a distal end portion 36a partially closed by wall 37. As shown in FIG. 8, the outer surface of catheter 36 adjacent the distal end portion 36a thereof is provided with standoff 38 having an apex 38a and a ramp 38b. The catheter has fiber optic 39 disposed therein. The fiber optic has a distal end portion 39a which is adapted to release laser energy into a blood vessel when the proximal end portion (not shown) of fiber optic 39 is connected to a source of laser energy external to the patient. The catheter device 35 also includes lumen 40 disposed within catheter 36 and having distal end portion 40a. The distal end portion of the lumen can be in the form of a crescent-shape as shown in FIG. 7.

Catheter device 35 also includes bladder 41 disposed adjacent the distal end portion 36a of the catheter and substantially opposite standoff 38. The bladder overlies port 42 to which is connected lumen 43. Lumen 43 when its proximal end portion (not shown) is connected to a fluid pressure source is adapted to inflate the bladder as shown in FIG. 9. Inflation of the bladder urges standoff 38 against the inner surface 19a of the blood vessel and the outer surface of the catheter 36 adjacent to the standoff 38. As a result, the distal end portion 36a of the catheter assumes the curved form shown in FIG. 9 with the result that the distal end 39a of the fiber optic is directed toward the center line of the blood vessel. In this position as shown in FIG. 9, the laser energy can be directed against plaque 28. With the application of negative pressure or vacuum to lumen 40, debris from the plaque enters the crescent-shaped opening 40a of the lumen and thereby is removed from the blood vessel.

As shown in FIG. 10, catheter 35 can be rotated about filament 44 in order to bring the laser energy emitted from fiber optic 39 substantially into alignment with plaque 28. In addition, the filament enables the catheter device 35 to be rotated throughout the inner circumference of the blood vessel in order to sweep the entire interior of the blood vessel with the laser energy.

Figure 13:
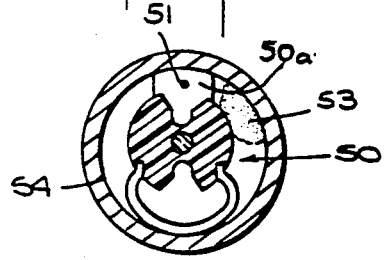
FIG. 13 is a vertical section showing the catheter of FIG. 12 positioned by the inflated bladder within a duct.

In FIG. 11, there is shown an embodiment of the catheter device 50 of the invention in which the means for intersecting and releasing undesired material from the interior of a duct of a patient, such as a biliary duct, a duct associated with the gall bladder, etc. Catheter device 50 includes a recess 50a in the outer wall of the catheter extending along the length of the catheter adjacent the distal end 50b thereof and a heating element 51 which can comprise resistance wire such as that of Nichrome wire. Leads 52 are adapted to deliver electrical energy to the heating element 51. Rotation of catheter 50 as shown in FIG. 13 enables the heating element to intersect and release undesired material 53 from the inner surface of duct 54.

Figure 12:
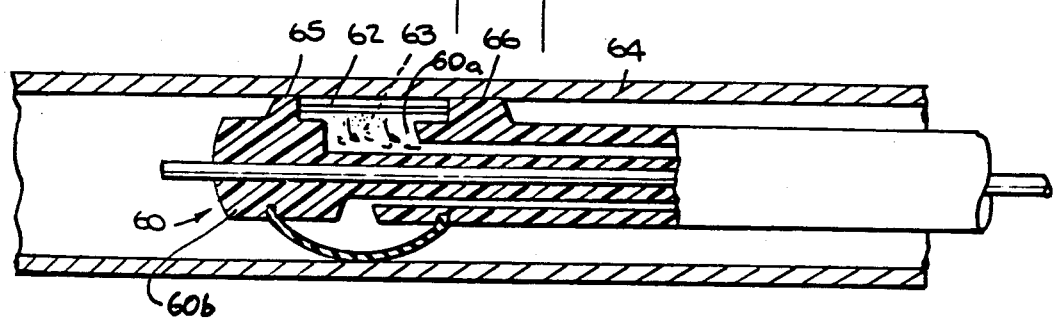
FIG. 12 is a fragmentary vertical section of still another embodiment of the catheter of the invention which includes a blade.
Figure 14:
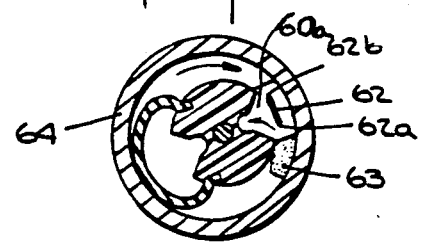
FIG. 14 is a vertical section view of the catheter of FIG. 13, showing the catheter of FIG. 12 being rotated within a duct.

In FIG. 12, there is shown an embodiment of the catheter device 60 of the invention in which there is provided a blade 62 for intersecting and releasing undesired material 63 from the inner surface of duct 64. Catheter device 60 includes distal end 60b and a recess 60a in the outer wall of the catheter adjacent the distal end 60b. Blade 62 as shown in FIG. 14 includes oppositely disposed edges 62a and 62b which are adapted to sever undesired material 63 as catheter device 60 is rotated within duct 64.

OPERATION

Prior to the use of the catheter device of the invention, the location of an undesired material such an occlusion or accumulation of plaque or other lesions within a duct such as a blood vessel of the patient is first determined by conventional techniques including angioscan, X-ray, tomography or the like. Thereafter, an incision can be made in the femoral artery, by way of example, and the filament 24 is then advanced through the artery to the vicinity of the occlusion or accumulation of plaque (FIG. 2). In the alternative, access to the region of a blockage can be attained during an operation, such for example, during open-heart surgery. Once the incision is made in the blood vessel in question, known techniques such as those involving fluroscopy or angioscopy can be used to observe the condition within the blood vessel which is to be treated by use of the catheter device of the invention. In this way, the catheter device is controlled to be advanced into the blood vessel in which the filament has been extended until the region to be treated is reached.

Fluid pressure is then applied to the bladder 29 of the device in order to position it with respect to the plaque to be removed. In the case of catheter device 20, bladder 29 urges abutments 22 and 23 against the inner surface of the blood vessel 19 and places the device in preparation for the introduction of laser energy. In the case of catheter device 35, inflation of bladder 41 causes standoff 38 as well as the outer surface 36b of the catheter adjacent the standoff to come into contact with the inner surface of the blood vessel, thereby causing the distal end portion of the catheter device 35 to assume a curved position within the blood vessel.

At this point, reduced pressure is applied to suction port 31, in the case of catheter device 20, or opening 40a, in the case of the catheter device 35. Laser energy in the form of pulses, bursts or cycles of application is then applied to catheter devices 20 and 35. In the case of device 20, the laser energy vaporizes plaque 28 disposed between the abutments 22 and 23. As the plaque is vaporized, abutment 22 and 23 prevent the escape of laser energy into the blood vessel adjacent the distal end portion of the catheter.

In catheter device 35 the arcuate form of the catheter device, resulting from the inflation of bladder 41, causes the laser energy to be directed toward the center line of the blood vessel (FIG. 9). As a result, the laser energy is dissipated in the central region of the blood vessel as the plaque is vaporized, thereby preventing undesired contact of the laser energy with the inner surface 19a of the blood vessel.

The operator of the catheter device of the invention can determine when the procedure of removal of an occlusion or plaque has been completed by fluorscopic observation or by taking a pressure gradient observation across the lesion. It should be understood that during use of the catheter device of the invention, the blood vessel being treated can remain under observation by known techniques such as the use of endoscopes, angioscan, tomography or the like. In addition, the catheter device of the invention can be rotated by the operator with respect to the filament during use to effect a sweep of the interior of a blood vessel in carrying out the procedure.

In the catheter device 50, electrically heated element 51 can be used to sever undesired material from between abutments 55 and 56. In the catheter device 54, blade 62 can be used to sever and release undesired material disposed between abutments 65 and 66.

What is claimed is:

1. A catheter device for use in removing undesired material from a duct within a patient's body comprising:
    a catheter adapted to be inserted within a duct in the patient's body, the catheter having a proximal end portion and a distal end portion,
    means disposed adjacent the exterior of the catheter and the distal end portion of the catheter for severing undesired material from the interior of the duct in a patient's body when the distal end portion of the catheter is disposed adjacent to the undesired material, the severing means including an element adapted to be heated, and means for heating the element, the element when heated being adapted to sever the undesired material from the interior of the duct,
    an inflatable bladder mounted on the catheter adjacent the distal end portion thereof disposed substantially opposite the severing means, and
    means for controllably inflating the bladder when the device is disposed in the duct to enable the inflated bladder to contact the inner surface of the duct and urge the distal end portion of the catheter against the inner surface of the duct adjacent thereto,
    whereby the means for severing undesired material is positioned adjacent to the inner surface of the duct.

2. A catheter device in accordance with claim 1 and further comprising a pair of abutments extending radially from the outer surface of the catheter and spaced apart from one another along the length of the catheter adjacent the distal end portion thereof, the severing means being mounted between the pair of abutments, the bladder when inflated being adapted to urge the pair of abutments against the inner surface of the duct.

3. A catheter device in accordance with claim 1 and further comprising a lumen havng a proximal end and a distal end disposed within the catheter, the proximal end of the lumen being adapted to be connected to a source of reduced pressure less than the ambient pressure, the distal end of the lumen having a port disposed adjacent to the severing means, the port being adapted to receive undesired material when connected to the source of reduced pressure.

4. A catheter device in accordance with claim 1 and further comprising a filament extending along the length of the catheter to adjacent the distal end of the catheter, the catheter being rotatably disposed about the filament and adapted to be translated and rotated with respect to the filament, whereby the catheter is adapted to be positioned and to be rotated within the duct.

5. A catheter device for use in removing undesired material from a duct having an inner surface within a patient's body comprising:
    a catheter adapted to be inserted within a duct in the patient's body, the catheter having a proximal end portion and a distal end portion, the catheter adjacent the distal end portion having a recess extending along the length thereof, an elongated severing element being disposed within the recess adjacent the exterior of the catheter and extending in the direction of the length of the catheter for severing undesired material from the interior of the duct in the patient's body when the distal end portion of the catheter is disposed adjacent to the undesired material and the length of the catheter is rotated within the length of the duct, the elongated severing element when positioned approximately adjacent to the inner surface of the duct having no contact with the inner surface of the duct,
    an inflatable bladder mounted on the catheter adjacent the distal end portion thereof and disposed substantially opposite the elongated severing element and,
    means for controllably inflating the bladder when the device is disposed in the duct to enable the inflated bladder to contact the inner surface of the duct and urge the surface of the distal end portion of the catheter adjacent the recess against the inner surface of the duct adjacent thereto, and
    whereby the elongated severing element is adapted to be positioned adjacent to the inner surface of the duct and the undesired material thereon for removing of the undesired material upon rotation of the catheter.

6. A catheter device in accordance with claim 5 and further comprising a lumen having a proximal end portion and distal end portion disposed within the catheter, the proximal end portion of the lumen being adapted to be connected to a source of reduced pressure less than the ambient pressure, the distal end portion of the lumen having a port disposed adjacent to the elongated severing element, the port being adapted to receive undesired material when connected to the source of reduced pressure.

7. A catheter device in accordance with claim 5 further comprising a filament extending along the length of the catheter to adjacent the distal end portion of the catheter, the catheter being rotatably mounted about the filament and adapted to be translated and rotated with respect to the filament, whereby the catheter is adapted to be positioned and to be rotated within the duct.

8. A method for removing undesired material from a duct an inner surface within a patient's body by use of a catheter adapted to be inserted within the duct in the patient's body, the catheter having a proximal end portion and a distal end portion, the catheter adjacent the distal end portion having a recess extending along the length thereof, an elongated severing element disposed within the recess adjacent the exterior of the catheter and extending in the direction of the length of the catheter for severing undesired material from the interior of the duct in a patient's body when the distal end portion of the catheter is disposed adjacent to the undesired material and the length of the catheter is rotated within the length of the duct, the elongated severing element within the recess when positioned approximately adjacent to the inner surface of the duct being spaced apart from the inner surface of the duct, and an inflatable bladder mounted on the catheter adjacent the distal end portion thereof disposed substantially opposite the recess and the elongated severing element therein, the method comprising the steps of:
placing the distal end portion of the catheter adjacent the undesired material,
controllably inflating the bladder when the recess in the distal end portion of the catheter is adjacent the undesired material to enable the inflated bladder to contact the inner surface of the duct and urge the recess in the distal end portion of the catheter adjacent the inner surface of the duct adjacent thereto, and
operating the elongated severing element when the recess is positioned adjacent to the inner surface of the duct at the undesired material such that the elongated severing element contacts and substantially severs the undesired material without contacting the inner surface of the duct.

9. A method in accordance with claim 8 in which the step of operating the elongated severing element comprises rotating the elongated severing element with respect to the undesired material.

10. A method in accordance with claim 8 wherein the catheter has a lumen with a proximal end portion and a distal end portion disposed within the cathether, the proximal end portion of the lumen being adapted to be connected to a source of reduced pressure less than the ambient pressure, the distal end portion of the lumen having a port disposed adjacent to the elongated severing element and further comprising the step of applying reduced pressure to the port to cause the undesired material to be received into the lumen.

11. A method in accordance with claim 8 wherein the catheter has a filament extending along the length of the catheter to adjacent the distal end portion of the catheter, the catheter being rotatably disposed about the filament and adapted to be translated and rotated with respect to the filament and further comprising the step of positioning the catheter by rotating and translating the catheter within the duct.

12. A method of removing undesired material from a duct within a patient's body by use of a catheter adapted to be inserted within the duct, the catheter having a proximal end portion and a distal end portion and a pair of abutments extending radially from the outer surface of the catheter and spaced apart from one another along the length of the catheter adjacent the distal end portion thereof, the pair of abutments being adapted to form a chamber therebetween when the pair of abutments are adjacent the inner surface of the duct, an elongated severing element disposed between the pair of abutments for severing undesired material from the interior of the duct, and an inflatable bladder mounted on the catheter adjacent the distal end portion thereof and substantially opposite the elongated severing element, the method comprising the steps of:
positioning the chamber formed between the pair of abutments adjacent the undesired material within the duct,
inflating the inflatable bladder to urge the abutments against the inner surface of the duct adjacent the undesired material; and
rotating the catheter to enable the elongated severing element to sever the undesired material.

13. A method in accordance with claim 12 and further comprising a lumen having a proximal end portion and a distal end portion disposed within the catheter, the proximal end portion of the lumen being adapted to be connected to a source of reduced pressure less than the ambient pressure, the distal end portion of the lumen having a port disposed adjacent to the elongated severing element and further comprising the step of applying reduced pressure to the port to cause the undesired material to be received into the lumen.

14. A method in accordance with claim 12 and further comprising a filament extending along the length of the catheter to adjacent the distal end portion of the catheter, the catheter being rotatably disposed about the filament and adapted to be translated and rotated with respect to the filament and further comprising the step of positioning the catheter by rotating and translating the catheter within the duct.

* * * * *

UNITED STATES PATENT AND TRADEMARK OFFICE
CERTIFICATE OF CORRECTION

PATENT NO. : 4,685,458

DATED : August 11, 1987

INVENTOR(S) : LECKRONE

It is certified that error appears in the above-identified patent and that said Letters Patent is hereby corrected as shown below:

Column 1, line 45, delete "ooclusion" and insert --occlusion--;

Column 8, line 54, delete "duct an" and insert --duct having an--;

Column 9, line 28, delete "cathether" and insert --catheter--.

Signed and Sealed this

Twenty-ninth Day of March, 1988

Attest:

DONALD J. QUIGG

*Attesting Officer*    *Commissioner of Patents and Trademarks*